United States Patent [19]
Keller

[11] Patent Number: 5,902,339
[45] Date of Patent: May 11, 1999

[54] METHOD AND DEVICE FOR INSERTING AND POSITIONING A PROSTHESIS

[75] Inventor: Arnold Keller, Kayhude, Germany

[73] Assignee: Waldemar Link (GmbH & Co), Germany

[21] Appl. No.: 08/914,710

[22] Filed: Aug. 19, 1997

[30] Foreign Application Priority Data

Aug. 19, 1996 [DE] Germany ........................ 296 14 349 U

[51] Int. Cl.⁶ ................................. A61F 2/38; A61F 2/46
[52] U.S. Cl. ................................. 623/20; 606/88; 606/99
[58] Field of Search ................................ 606/88, 86, 99; 623/20, 16, 66

[56] References Cited

U.S. PATENT DOCUMENTS

| | | | |
|---|---|---|---|
| 3,715,763 | 2/1973 | Link ........................................... | 623/20 |
| 4,034,418 | 7/1977 | Jackson et al. ........................... | 623/20 |
| 4,211,228 | 7/1980 | Cloutier .................................... | 623/20 |
| 5,059,196 | 10/1991 | Coates ..................................... | 606/99 |
| 5,417,693 | 5/1995 | Sowden et al. ........................... | 606/99 |
| 5,520,695 | 5/1996 | Luckman ................................. | 606/88 |
| 5,645,602 | 7/1997 | Albrektsson et al. ..................... | 623/20 |

FOREIGN PATENT DOCUMENTS 2691355 11/1993 France ..................................... 623/20

OTHER PUBLICATIONS

Eftekhar II Knee Prosthesis, pp. 1–13.

*Primary Examiner*—Mickey Yu
*Assistant Examiner*—Bruce E. Snow
*Attorney, Agent, or Firm*—Medlen & Carroll, GSM LLP

[57] ABSTRACT

The present invention provides a device and a method which allows a femoral sliding knee endoprosthesis to be inserted with the condylar slide surface parts correctly positioned in relation to each other. An insertion appliance comprising a locking mechanism locks the unconnected prosthesis parts in place until completion of the insertion procedure.

10 Claims, 1 Drawing Sheet

METHOD AND DEVICE FOR INSERTING AND POSITIONING A PROSTHESIS

FIELD OF INVENTION

This invention relates to the field of prostheses, and in particular to a device and method of inserting a femoral sliding knee endoprosthesis.

BACKGROUND

To replace the femoral condylar slide surfaces of the knee joint, slide surface prostheses are known which are designed relatively thin and thus require only minimal resection of the cartilage and bone material, and in some cases permit partial or complete preservation of the hard cortical bone. The prosthetic slide surfaces which are assigned to the two condyles are generally connected by way of a scutiform part which protrudes upwards on the anterior aspect and forms a slide surface for the patella. Such a connection of the condylar slide surfaces ensures that they are positioned correctly matching each other. In many cases, it is not necessary to replace the patellar slide surface. A simpler connection of the two condylar slide surfaces would then be sufficient. However, experience has shown that a simpler connection is often unable to cope with the loads arising during use and so breaks. Instead of this, it is possible to employ unconnected condylar slide surfaces, but these have the disadvantage that their correct mutual positioning is not really possible without manual intervention.

An instrument is known (cf. brochure "Schalen-Kniegelenkprothesensystem SKI" from the company Interplanta GmbH, Hamburg) which is used for inserting mutually positioned tibial plateaus and which has two mutually parallel pins which can each be introduced into a bore in one of the plateaus, and two spikes which run transverse to these pins and engage in each case in a transverse bore. Such a solution is not feasible in the case of condylar slide surface prostheses, mainly because the position of the slide surface does not permit provision of the said bores.

SUMMARY OF THE INVENTION

The present invention provides methods and devices for inserting a femoral sliding knee endoprosthesis. The invention makes available a device which allows a femoral sliding knee endoprosthesis to be inserted with the condylar slide surface parts correctly positioned in relation to each other.

The invention assumes the use of unconnected slide surface prosthesis parts. The correct mutual positioning of these parts is ensured by means of suitably aligned holding arrangements in an insertion instrument which forms two receiving seats for the prosthesis parts. These are equipped with holding elements matching the holding parts of the insertion appliance. These holding elements consist in each case of a pair of tracks preferably arranged approximately in the AP direction (anterior-posterior direction). This is the direction which, with the knee extended, runs from the front rearwards, in other words in a sagittal plane perpendicular to the direction of the femur. This feature allows the instrument with the U-shaped receiving seats to be withdrawn in the anterior direction after the prosthesis parts have been inserted.

The pairs of tracks are expediently provided on both sides of the receiving seats and the prosthesis parts. However, static precision is also afforded when a pair of tracks is arranged only on one side of the receiving seats and of the prosthesis parts, while the other side is provided with a punctiform or otherwise shaped holding arrangement. For example, a bore or dimpled indentation can be provided on the edge of the prosthesis part, into which bore or indentation there engages the tip of a screw which is provided on the receiving seat and which is unscrewed in order to free the appliance from the prosthesis parts.

In each case, i.e. also when the track arrangements are provided on both sides, a locking mechanism should be provided which will ensure that the prosthesis parts retain their correct starting position until completion of the insertion procedure. This locking mechanism can be formed, for example, by a tightening screw provided on each of the receiving seats.

Although, in the present context, reference is made in general to guide tracks, this is intended to signify all configurations which necessarily align the prosthesis parts and make it possible to withdraw the appliance from the implanted prosthesis parts in one direction. At least one guide track of each pair of tracks is preferably formed by a substantially continuous groove or ledge. In the other part it is then sufficient to suggest the track by means of a plurality of projections. If, for example, the track on the edge of the prosthesis part is designed as a continuous groove, it will suffice, in the receiving seat, to have two projections engaging into the groove at a distance from one another. Or if the track on the receiving seat is formed by a continuous ledge, it will suffice, on the edge of the prosthesis part, to have two pair pins, or two pints arranged at a distance from one another on one side of the ledge, and one pin arranged approximately centrally thereto on the other side of the ledge. Nor does the respective other track have to be designed continuous; instead; it can be interrupted at those located where cooperation with corresponding elements on the other part is not necessary. Suggesting one of the two tracks by means of individual projections also has the advantage that the desired alignment of the prosthesis parts in relation to the insertion appliance then exists only when the prosthesis parts are fixed correctly in the insertion position in the appliance. It ends immediately after the operator has begun to remove the appliance from the inserted implants, which reduced the risk of awkward movement, during removal of the appliance, dislodging the implants from their intended position.

The device according to the invention is primarily intended for those prostheses which are anchored by means of bone cement. Until the cement has set, the prosthesis parts are kept correctly aligned with each other by means of the insertion appliance.

DESCRIPTION OF THE INVENTION AND EMBODIMENTS

This invention relates to the field of prostheses, and in particular to a device and method of inserting a femoral sliding knee endoprosthesis. The invention is explained in greater detail with reference to illustrative embodiments.

Figure 1:
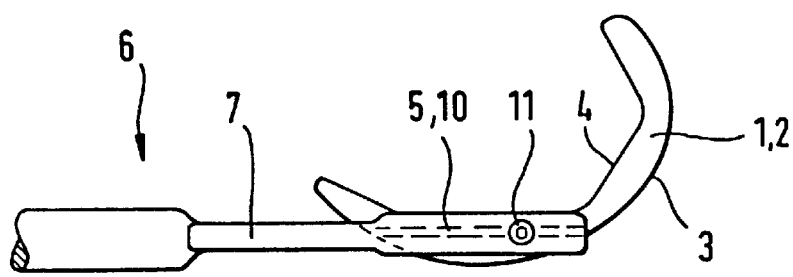
FIG. 1 shows a side section of the appliance, with prosthesis parts fixed therein.
Figure 2:
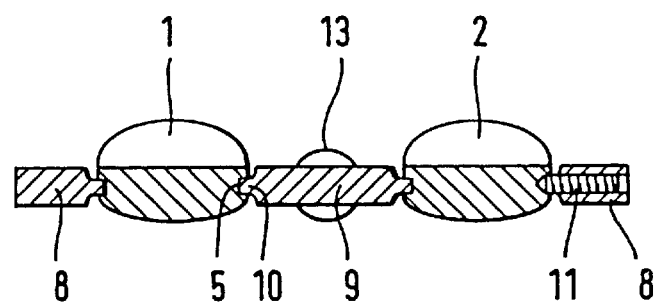
FIG. 2 shows a front section of FIG. 1.

In one embodiment, the knee prosthesis to be inserted consists of the prosthesis parts 1, 2, which can be seen in side view in FIG. 1 and which have a slide surface 3, and also a surface 4 which is to be connected to the bone. They can also have studs or other surface structure (not shown) which improve the anchoring in the bone and the adhesion to the cement. This example assumed that they coincide in side view and are to be inserted exactly parallel to one another. This need not be so.

The prosthesis parts 1, 2 are provided on both edges with grooves 5 which run parallel to each other in the AP direction. The insertion instrument 6 has a twin fork 7 with two outer prongs 8 and a middle prong 9, with the prosthesis parts 1, 2 fitting into the spaces between these prongs. Provided in the front section of the prongs 8, 9, on their side faces facing each other, there are protruding ledges 10 whose dimensions are matched to the grooves 5 of the prosthesis parts and which likewise run parallel to each other. The prosthesis parts 1, 2 can therefore be pushed, in each case between a pair of prongs 8, 9, onto the ledges 10 via their grooves 5. These form the above-mentioned, cooperating guide tracks.

Figure 3:
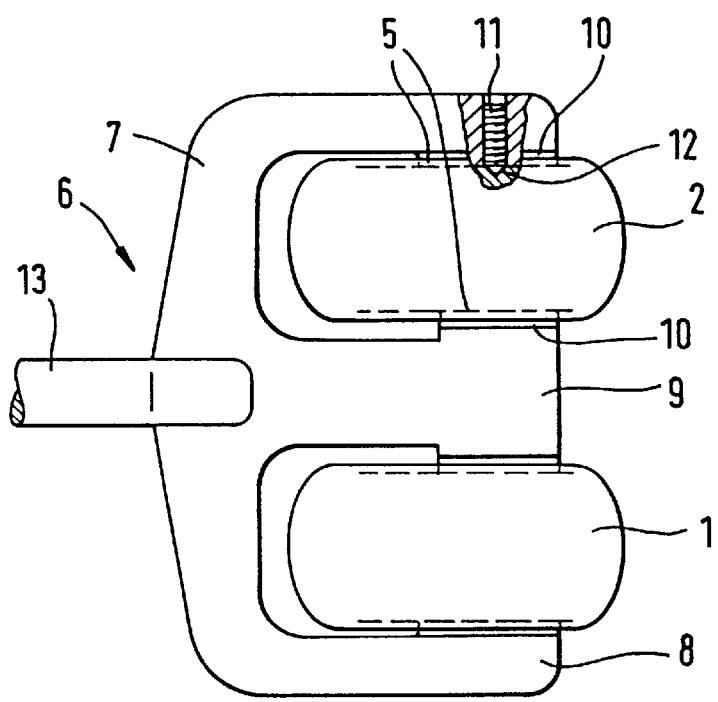
FIG. 3 shows a plan view of FIG. 1.

The two outer prongs 8 each contain a grub screw 11 whose tip, as is shown at the top in FIG. 3, engages in a corresponding conical bore 12 in the associated prosthesis part and thereby secures the latter in the correct insertion position on the insertion appliance 6.

The insertion appliance 6 has a shaft 13 on which a handle (not shown) is provided. The longitudinal direction of the shaft 13 and of the insertion appliance overall coincides essentially with the direction of the ledges 10.

The appliance allows the two prosthesis parts to be inserted together in an exact mutual alignment and to be held in the intended position until the bone cement securing them has set. The grub screws 11 are then unscrewed and the appliance can be withdrawn in a movement in the anterior direction. It will be seen from the drawing that it can be designed very flat and therefore takes up only a little space in the operating field.

I claim:

1. A prosthetic system comprising:
   an insertion instrument comprising two receiving seat; and two unconnected condylar prosthesis parts, each of said receiving seats and each of said condylar prosthesis parts comprising left and right side edges, and each of said receiving seats and each of said condylar prosthesis parts cooperating via at least one pair of guide tracks, of which one guide track is arranged on at least one of said side edges of said condylar prosthesis parts, and further comprising a locking mechanism for locking the position of said condylar prosthesis parts in said receiving seats wherein said locking mechanism comprises a tightening screw provided on each of said receiving seats.

2. The prosthetic system of claim 1, wherein in that the guide tracks run approximately parallel to each other.

3. The prosthetic system of claim 1, wherein said at least one pair of guide tracks are provided on said left and right side edges of the receiving seats and prosthesis parts.

4. A method of inserting a prosthesis in a knee of a subject, comprising:
   a) providing: i) a prosthesis insertion appliance comprising two receiving seats, each of said receiving seats having guide tracks and one position locking means, ii) two unconnected condylar prosthesis parts, said prosthesis parts comprising means for cooperating with said guide tracks of said receiving seats, iii) anchoring means and iv) a knee of a subject;
   b) placing said two unconnected condylar prosthesis parts on said guide tracks of said receiving seats of said insertion appliance;
   c) locking each of said two condylar prosthesis parts into desired positions with said position locking means so as to create an insertion appliance with positioned condylar prosthesis parts;
   d) inserting said insertion appliance with positioned condylar prosthesis parts into said knee of said subject;
   e) anchoring said positioned prosthesis parts to said knee with said anchoring means so as to create anchored prosthesis parts; and
   f) freeing said anchored prosthesis parts from said insertion appliance.

5. The method of claim 4, wherein said position locking means comprises a tightening screw.

6. The method of claim 4, wherein said anchoring means comprises bone cement and said position locking means causes the prosthesis parts to retain their desired position until said cement has set.

7. A method of inserting a prosthesis in a knee of a subject, comprising:
   a) providing: i) a prosthesis insertion appliance comprising two receiving seats, and two unconnected condylar prosthesis parts, each of said receiving seats and each of said condylar prosthesis parts comprising left and right side edges, and each of said receiving seats and each of said condylar prosthesis parts cooperating via at least one pair of guide tracks, of which one guide track is arranged on at least one of said side edges of said condylar prosthesis parts; ii) anchoring means and iii) a knee of a subject;
   b) positioning said two unconnected condylar prosthesis parts on said guide tracks of said receiving seats of said insertion appliance;
   c) inserting said insertion appliance with positioned condylar prosthesis parts into said knee of said subject;
   d) anchoring said positioned prosthesis parts to said knee with said anchoring means so as to create anchored prosthesis parts;
   e) freeing said anchored prosthesis parts from said insertion appliance, and
   f) withdrawing said insertion appliance from said knee.

8. The method of claim 7, wherein the guide tracks run approximately in the AP direction relative to a sagittal plane, said sagittal plane being perpendicular to a femur of said subject.

9. The method of claim 7, wherein said at least one pair of guide tracks are provided on said left and right sides of the receiving seats and prosthesis parts.

10. The method of claim 7, wherein said device further comprises a locking mechanism for locking the position of said prosthesis parts in said receiving seats prior to said inserting of step (c).

* * * * *